(12) United States Patent
Sorebo

(10) Patent No.: US 6,679,104 B2
(45) Date of Patent: Jan. 20, 2004

(54) MATCHED MATERIAL COMBINATIONS FOR ABSORBENT ARTICLES AND THE LIKE

(75) Inventor: Heather Sorebo, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 200 days.

(21) Appl. No.: 10/029,130

(22) Filed: Dec. 20, 2001

(65) Prior Publication Data

US 2003/0120234 A1 Jun. 26, 2003

(51) Int. Cl.$^7$ .............................. G01N 5/02; A61F 13/20
(52) U.S. Cl. .......................... 73/73; 604/358; 604/361; 604/379
(58) Field of Search .................. 73/73, 865.6; 604/358, 604/361, 379

(56) References Cited

U.S. PATENT DOCUMENTS

| | | |
|---|---|---|
| 4,798,603 A | 1/1989 | Meyer et al. |
| 5,248,309 A | 9/1993 | Serbiak et al. |
| 5,368,926 A | 11/1994 | Thompson et al. |
| 5,505,719 A | 4/1996 | Cohen et al. |
| 5,556,392 A | 9/1996 | Koczab |
| 5,569,226 A | 10/1996 | Cohen et al. |
| 5,820,973 A | 10/1998 | Dodge, II et al. |
| 5,879,343 A | 3/1999 | Dodge, II et al. |
| 5,883,231 A | 3/1999 | Achter et al. |
| 5,931,823 A | 8/1999 | Stokes et al. |
| 5,994,615 A | 11/1999 | Dodge, II et al. |
| 6,060,638 A | 5/2000 | Paul et al. |
| 6,097,297 A * | 8/2000 | Fard .......................... 340/604 |
| 6,152,904 A | 11/2000 | Matthews et al. |
| 6,168,849 B1 | 1/2001 | Braverman et al. |
| 6,200,250 B1 * | 3/2001 | Janszen ..................... 493/383 |

FOREIGN PATENT DOCUMENTS

| | | |
|---|---|---|
| EP | 0359501 B1 | 12/1994 |
| EP | 0953324 A1 | 11/1999 |
| WO | WO 9723182 | 7/1997 |
| WO | WO 9740793 | 11/1997 |

* cited by examiner

*Primary Examiner*—Hezron Williams
*Assistant Examiner*—Katina Wilson
(74) *Attorney, Agent, or Firm*—Dority & Manning

(57) ABSTRACT

An in-vitro method is provided for determining an optimal combination of materials with respect to a particular menstrual flow condition for use in a feminine care absorbent article. The method involves using a simulated menstrual fluid at a controlled subject flow rate that corresponds to an actual menstrual flow condition, and observing the performance of different material combinations in the in-vitro test as an indication of their respective performance in actual use.

21 Claims, 1 Drawing Sheet

MATCHED MATERIAL COMBINATIONS FOR ABSORBENT ARTICLES AND THE LIKE

FIELD OF INVENTION

The present invention relates to adapting the functionality of nonwoven and other materials, suitable for use as components of an absorbent article, to enhance the liquid intake performance of such absorbent article. More specifically, this invention relates to determining optimal combinations of layer materials of an absorbent article for particular flow rate conditions to provide an improved absorbent article designed for specific flow conditions.

BACKGROUND OF THE INVENTION

Absorbent articles, particularly feminine hygiene products such as sanitary napkins and liners, are designed to absorb and contain body exudates. Such disposable products generally are single-use items which are discarded after a relatively short period of use—usually a period of hours—and are not intended to be washed and reused. Such articles usually are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The absorbent structure may include a number of different types of absorbent materials and layers, including a surge layer subjacent to and in liquid communicating contact with the bodyside liner, and an absorbent core typically formed of a blend or mixture of cellulosic pulp fluff fibers and absorbent gelling particles subjacent to and in liquid communicating contact with the surge layer. A transfer or distribution material layer may be provided between the surge layer and the absorbent core.

Desirably, personal care absorbent articles exhibit low leakage from the product and a dry feel for the wearer. Unfortunately, traditional feminine care products are not always adequate in preventing leakage for women that experience extremely heavy, heavy, and gush flow. It has been estimated that 60% or more of women with extremely heavy and heavy flow experience leakage with current feminine care sanitary pads. Leakage can result from a variety of performance deficiencies in the design of the product, or individual materials within the product. One cause of such leakage is an insufficient rate of liquid intake into the cover with subsequent transfer to the absorbent core, which functions to absorb and retain body exudates.

The liquid intake of a given absorbent product, and particularly the liner and surge materials forming the absorbent product, should thus be able to accept the expected liquid delivery rate into the absorbent product. The inability of the absorbent product to rapidly uptake liquid can result in excessive pooling of liquid on the body-facing surface of the bodyside liner before the liquid is taken up by the absorbent structure. Such pooled liquid can wet the wearer's skin and can leak from around the sides or edges of the absorbent article, causing discomfort, potential skin health problems, as well as soiling of the outer clothing or bedding of the wearer.

One approach to improve overall liquid intake of absorbent articles has focused on the bodyside liner and its capacity to rapidly pass liquid to the subjacent absorbent structure. Nonwoven materials, including bonded carded webs and spunbond webs, have been widely used as bodyside liners. Such nonwoven materials generally are intended to be sufficiently open and/or porous to allow liquid to pass through rapidly, while also functioning to keep the wearer's skin separate from the wetted absorbent underlying the liner. Attempts to improve the liquid intake of liner materials have included, for example, aperturing the liner material, treating the fibers forming the liner material with surfactants to enhance the wettability of the liner, and altering the durability of such surfactants.

Yet another approach has been to focus on various materials or layers placed between the bodyside liner and absorbent core material to enhance the core's ability to rapidly intake fluid and to provide separation between the absorbent core and the bodyside liner adjacent the wearer's skin. Such additional layer or layers, commonly referred to as a "surge" layer, can suitably be formed of thick, lofty nonwoven materials. Surge layers, particularly high loft, high bulk, compression resistant fibrous structures, provide a temporary retention or absorption function for liquid not yet absorbed into the absorbent core, which tends to reduce fluid flowback or re-wet from the absorbent core to the liner. A transfer or distribution material layer may be provided under the surge layer. This material is generally less hydrophilic than the other absorbent materials and is intended to spread liquid penetrating through the surge layer in the X-Y plane to more evenly distribute the fluid to the underlying absorbent core material.

Notwithstanding the foregoing, leakage in feminine care absorbent articles is still a problem, particularly for women experiencing heavy menstrual flows. The need exists for improvements in the liquid intake performance of the article materials, for example the liner materials and subjacent surge layer. In particular, there is a need for liner or cover materials that can provide improved handling of heavy liquid surges, particularly in feminine care products. The present invention relates to just such an improvement.

SUMMARY OF THE INVENTION

The present invention is directed to a protocol or test method for determining an optimal combination of materials for use in absorbent products, particularly feminine care products. The test method is particularly suited for improving the performance of feminine care products in heavy, extremely heavy, and gush menstrual flow conditions by optimizing materials selected for a particular menstrual flow condition.

The test method is based in part upon the realization that menstrual fluid is a complex, highly viscous, and non-homogeneous fluid and that traditional methods and parameters for measuring a material's ability to absorb or pass fluid are not an accurate or reliable predictor of the material's abilities with respect to menstrual fluid. The test method is also based on part upon the realization that accurate data can be obtained from in-vitro methods (i.e., lab or bench tests) under certain conditions and, thus, useful correlated data can be readily and quickly obtained. Traditional in-vivo tests are time consuming and may be misleading. For example, it is nearly impossible to predict or determine an actual menstrual flow rate of the women participating in the tests. There is no guarantee that a product intended to be tested for heavy menstrual flow conditions actually experienced such conditions, etc.

One embodiment of a test method according to the present invention for determining an optimal combination of materials for use in feminine care products under particular menstrual flow conditions includes an in-vitro method for determining an optimal combination of materials with respect to a particular menstrual flow condition for use in a feminine care absorbent article. The method includes selecting a subject flow rate corresponding to the average flow rate of menstrual fluid for a particular menstrual flow condition. A simulated menstrual fluid is provided to a flow rate controllable metering device, such as a syringe pump, and is dispensed onto a first combination of materials at the subject flow rate. The performance of the material combination is observed to determine if the particular combination adequately performs its intended purpose in the feminine care product at the subject flow rate. At least one of the materials in the combination is then changed and the steps of dispensing the simulated menstrual fluid and observing the performance of the combination of materials is again observed. Eventually, an optimal combination of the materials can be determined based on their performance when subjected to the simulated menstrual fluid at the subject flow rate.

The method may be used to determine the optimal material to be combined with a particular other material. For example, the test may be used to determine the optimal surge layer material to be used with a particular type of cover layer. In this instance, the cover material is held constant and the surge layer material is varied until the optimal surge material is determined.

Although the test method is particularly suited for determining an optimal combination of materials for use as a surge layer and cover layer for use in a feminine care product, it should be understood that the test is not limited to such a combination. For example, an optimal combination of absorbent core and surge layer materials may also be determined according to the inventive test method. Likewise, an optimal combination of cover layer and absorbent core materials may be determined.

Once the optimal combination of materials is selected for the subject flow rate, the flow rate may be changed to correspond to a different menstrual flow condition. It can then be determined how the combination of materials performs for different flow conditions. It may be that a combination of materials performs extremely well at a flow rate corresponding to a heavy menstrual flow, but performs poorly at light flow or extremely heavy flow conditions.

In an alternate embodiment, the test may be used to determine an optimal combination of materials only for a particular menstrual flow condition, for example an extremely heavy flow condition of about 20 ml/hr of menstrual flow, regardless of the combination's performance at other flow rates. This method may be used in designing a particular flow specific product, such as an overnight heavy flow product.

In still an alternate embodiment, the subject flow rate may be selected as representative of a wide range of flow conditions.

Particularly for feminine care products, the method may include selecting the optimal combination of materials based on the combination's ability to reduce leakage of the absorbent article, minimize wetness against a user's skin, and increase menstrual fluid intake.

The method according to the invention will be described in greater detail below with reference to specific embodiments.

DETAILED DESCRIPTION OF THE INVENTION

Figure 1:
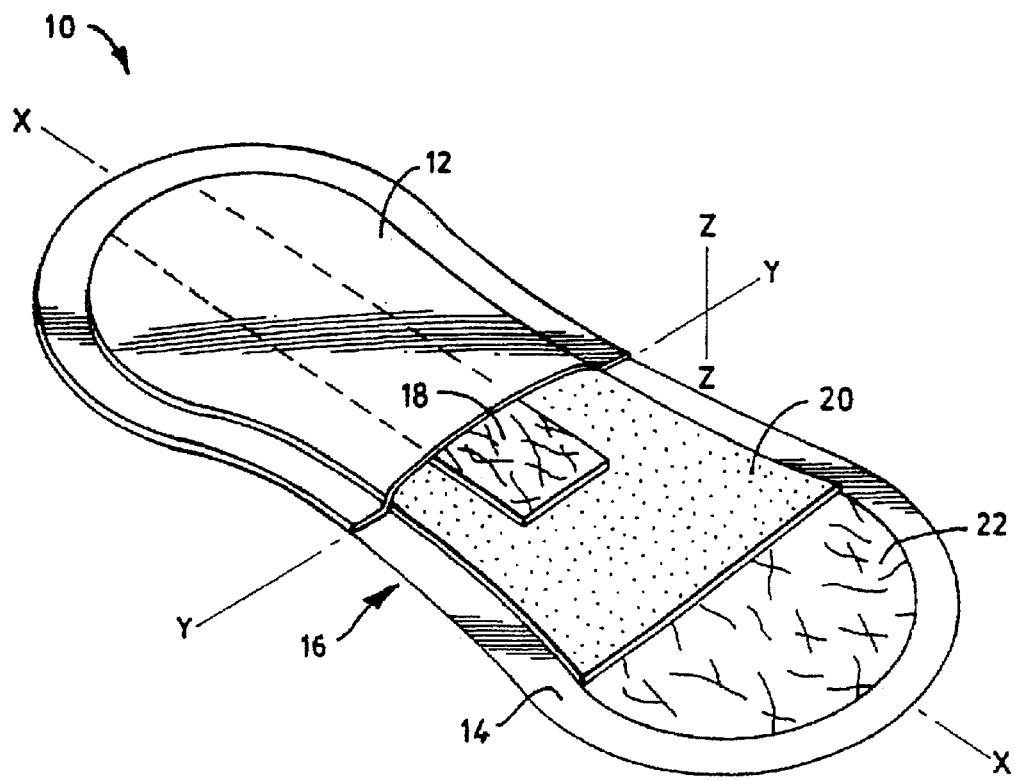
FIG. 1 is a partially cut away, perspective view of a feminine care absorbent article and particularly shows various layers of materials used in such articles.

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present inventive method is related to feminine care absorbent articles. A typical such article is illustrated in the figure as a sanitary napkin 10 having a generally racetrack shape. It should be appreciated though that the invention is not limited to any particular style, shape, or design of feminine care product. For example, the article may be a pantiliner, pantishield, or any other disposable absorbent article that is well known in the art, and can include other shapes, such as oval, hourglass, straight sided, wrapped and peripheral sealed constructions. It should also be noted that feminine care absorbent articles come in various sizes and shapes and vary in thickness. For example, in some embodiments, the absorbent article 10 is between about 150 mm to about 320 mm long, and between about 60 mm to about 120 mm wide and has a racetrack shape with rounded ends. Moreover, in some embodiments, the absorbent article has a thickness or caliper of less than about 5 mm, and in some embodiments, less than about 4 mm.

In the illustrated embodiment, the absorbent article 10 includes a bodyside liner or cover 12, an outer cover 14, and an absorbent structure 16 positioned between the cover 12 and outer cover 14.

The bodyside cover 12 is generally designed to contact the body of the user and is liquid-permeable. The cover 12 can surround the absorbent core structure 16 so that it completely encases the absorbent article 10. Alternatively, the cover 12 and the and outer cover 14 can extend beyond the absorbent core structure 16 and be peripherally joined together, either entirely or partially, using known techniques. Typically, the bodyside cover 12 and the outer cover 14 are joined by adhesive bonding, ultrasonic bonding, or any other suitable joining method known in the art.

The cover 12 is liquid-permeable, sanitary, clean in appearance, and somewhat opaque to hide menstrual fluid discharges collected in and absorbed by the absorbent core structure 16. The cover 12 further exhibits good strike-through and rewet characteristics permitting menstrual fluid discharges to rapidly penetrate through the cover 12 to the absorbent core structure 16, but not allow the fluid to flow back through the cover 12 to the skin of the wearer. Various materials can be used in forming the bodyside cover 12 of the present invention, including apertured plastic films, woven fabrics, nonwoven webs, apertured nonwoven webs, porous foams, reticulated foams and the like. It should also be appreciated that the bodyside cover 12 may include multiple layers of the same or different materials, such as a dual-layer material including laminates and the like. The only requirement of the bodyside cover 12 is that it can be matched to or coordinated with the subjacent layer of the absorbent structure to achieve the required improvement in liquid intake performance described herein.

Nonwoven materials have been found particularly suitable for use in forming the bodyside liner of the present invention, including spunbond or meltblown webs of polyolefin filaments, or bonded carded webs of natural (for example, wood or cotton fibers) and/or synthetic (for example, polypropylene or polyester) fibers. For example, in the embodiment shown, bodyside cover 12 can be a nonwoven spunbond web of synthetic polypropylene filaments having a fiber size ranging from about 12 to about 48 microns, and more particularly from about 18 to about 43 microns. The nonwoven web can have a basis weight ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such nonwoven web can be from about 150 darcy to about 5000 darcy, and more particularly from about 850 darcy to about 1800 darcy. The nonwoven web can be surface treated with a selected amount of surfactant, such as about 0.28% Triton X-102 surfactant, or otherwise processed to impart the desired level of wettability and hydrophilicity. It is considered desirable for purposes of the present invention for the nonwoven or other material utilized as a liner 12 to have at least the same, or a greater, level or degree of wettability and hydrophilicity as the subjacent layer of the absorbent structure 16. If a surfactant is used, it can be applied to the web by any conventional means, such as spraying, printing, brush coating and the like.

The outer cover 14 is typically formed of a thin thermoplastic film, such as polyethylene film, which is substantially impermeable to liquid. Outer cover 14 functions to prevent body exudates contained in absorbent structure 16 from wetting or soiling the wearer's clothing, bedding, or other materials contacting the article 10. In the embodiment shown, for example, outer cover 14 can be a polyethylene film having an initial thickness of from about 0.5 mil (0.012 millimeter) to about 5.0 mil (0.12 millimeter). The polymer film outer cover 14 may be embossed and/or matte finished to provide a more aesthetically pleasing appearance. Other alternative constructions for the outer cover 14 include woven or nonwoven fibrous webs that have been constructed or treated to impart the desired level of liquid impermeability, or laminates formed of a woven or nonwoven fabric and thermoplastic film. Outer cover 14 may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

Disposed between the bodyside cover 12 and outer cover 14 is an absorbent structure 16, which includes a surge layer 18 and an absorbent core 22. A transfer or distribution layer 20 may also be disposed between the surge layer 18 and absorbent core layer 22.

The absorbent core material 22 suitably can be formed of a blend of hydrophilic cellulosic wood pulp fluff fibers and/or highly absorbent gelling particles (e.g., superabsorbent). The absorbent core 22 is generally compressible, conformable, non-irritating to the wearer's skin, and capable of absorbing and retaining liquid body exudates. For purposes of this invention, the absorbent core 22 can comprise a single, integral piece of material, or a plurality of individual separate pieces of material. The size and absorbent capacity of absorbent core 22 should be compatible with the size of the intended user and the liquid loading imparted by the intended use of the article 10.

The surge layer 18 serves to quickly collect and temporarily hold menstrual fluid, to transport such fluid from the point of initial contact and spread the fluid to other parts of the surge layer, and then to eventually release such fluid into the subjacent layers of the absorbent structure 16. The surge layer 18 is most typically interposed between and in intimate, liquid communicating contact with the bodyside cover 12 and the absorbent core layer 22, although other additional layers may be incorporated into the overall product design, including a transfer layer 20 as described below, if so desired. To further enhance liquid transfer, it can be desirable to attach the upper and/or lower surfaces of the surge layer 18 to the cover 12 and/or to the subjacent layer of the absorbent structure 16. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, surge layer 18 is adhesively bonded to the bodyside cover 12, the amount of adhesive add-on should be sufficient to provide the desired level(s) of bonding, without excessively restricting the flow of menstrual fluid from the cover into the surge layer.

The surge layer 18 represents a significant absorbing portion of the absorbent article 10 and has the capability of absorbing at least about 75%, particularly about 80%, and more particularly about 90% of the menstrual fluid deposited onto the absorbent article 10. The surge layer 18 can generally have any shape and/or size desired. For example, in one embodiment, the surge layer 18 has a rectangular shape, with a length equal to or less than the overall length of the absorbent article 10, and a width less than the width of the absorbent article 10. Typically, the surge layer 18 is made of a material that is capable of rapidly transferring, in the z-direction, menstrual fluid that is delivered to the cover 12. Because the surge layer 18 is generally of a dimension narrower than the absorbent article 10, the sides of the surge layer 18 are spaced away from the longitudinal sides of the absorbent article 10 and the menstrual fluid is restricted to the area within the periphery of the surge layer 18 before it passes down and is absorbed into the subjacent layers.

Various woven fabrics and nonwoven webs can be used to construct surge layer 18. For example, the surge layer 18 may be a nonwoven layer composed of a meltblown or spunbond web of polyolefin filaments. Surge layer 18 also can be a bonded carded web or an airlaid web composed of natural and/or synthetic fibers. The bonded carded web may, for example, be a powder bonded carded web, an infrared bonded carded web, or a through-air bonded carded web. The infrared and through-air bonded carded webs can optionally include a mixture or blend of different fibers, and the fiber lengths within a selected web may range from about 6 mm to about 60 mm. The surge layer may be composed of a substantially hydrophobic material, and the hydrophobic material may optionally be treated with a surfactant or otherwise processed to impart a desired level of wettability and hydrophilidty. Surge layer 18 can have a generally uniform thickness and cross-sectional area.

The absorbent structure 16 may also include a distribution or transfer layer 20 disposed between the surge layer 18 and the absorbent core 22. In some embodiments, the transfer layer 20 contains a material that is less hydrophilic than the other absorbent members, and may generally be characterized as being substantially hydrophobic. For example, the transfer layer 20 may be a nonwoven fibrous web composed of a relatively hydrophobic material, such as polypropylene, polyethylene, polyester or the like, and also may be composed of a blend of such materials. One example of a material suitable for the transfer layer 20 is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer layer 20 are described in U.S. Pat. No. 4,798,603 to Meyer, et al. and U.S. Pat. No. 5,248,309 to Serbiak et al. The transfer layer 20 may also be treated with a selected amount of surfactant to increase its initial wettability.

The transfer layer 20 can generally have any size and, typically is approximately equal to the length of the absorbent article 10. The transfer layer 20 can also be equal in width to the surge layer 18, but is typically wider. The transfer layer 20 typically has a basis weight less than that of the other absorbent members. For example, the basis weight of the transfer layer 20 is typically less than about 150 grams per square meter (gsm), and in some embodiments, between about 10 gsm to about 100 gsm. In one particular embodiment, the transfer layer 20 is formed from a spunbonded web having a basis weight of about 30 gsm.

The above-described components of the absorbent article 10 may be assembled together in a variety of well-known absorbent article configurations by using a variety of conventional techniques known in the art. For example, the components may be attached to one another using thermal or ultrasonic bonding, adhesives, such as hot melt pressure-sensitive adhesives, and the like, as well as combinations of the foregoing or other appropriate attachment means. In the case of adhesive bonding, the adhesive can be applied using conventional methods, such as by spraying droplets or filaments of adhesive.

For purposes of the present description, "extremely light" menstrual flow is considered to be at about 0–2 ml/hr. "Light " menstrual flow is considered to be at about 2–4 ml/hr. "Medium" menstrual flow is considered to be at about 4–8 ml/hr. "Heavy" menstrual flow is considered to be at about 8–12 ml/hr. "Extremely heavy" menstrual flow is considered to be greater than about 12 ml/hr. "Gush" menstrual flow is considered to be at about at 2–4 ml over a period of about 1–5 sec, with an average flow of about 5 ml/sec.

The protocol or test method according to the invention is directed to a means for determining an optimal combination of materials discussed above for use in feminine care products. The test method is particularly suited for improving the performance of feminine care products in heavy, extremely heavy, and gush menstrual flow conditions by optimizing materials selected for a particular menstrual flow condition. The test method is based on part upon the realization that menstrual fluid is a complex, highly viscous, and non-homogeneous fluid, and that traditional methods and parameters for measuring a material's ability to absorb or pass fluid are not an accurate or reliable predictor of the material's abilities with respect to menstrual fluid. The test method is also based on part upon the realization that accurate data can be obtained from in-vitro methods (i.e., lab or bench tests) under certain conditions and, thus, useful correlated data can be readily and quickly obtained without resorting to in-vivo tests. Such data is particularly useful in predicting combinations of materials to reduce the chance of leakage and wetness, and to enhance the article's ability to rapidly intake fluid.

The method will be described for illustrative purposes only as a means to determine an optimal combination of materials for the cover layer 12 and surge layer 18. However, it should be appreciated that the method may be used to determine any optimal combination of materials used in the absorbent article 10. For example, an optimal combination of materials for the surge layer 18 and absorbent core 22 may be determined, or for the transfer layer 20 and absorbent core 22, etc.

The applicants realized that the complex nature of menstrual fluid may be an impediment to predicting the performance of the various materials based on traditional tests and material characteristics. For example, the mean percent area of a surge layer material is typically determined by surface porosity analysis and is generally used as an indicator of the material's ability to intake fluids, especially at lower flow rates (i.e., extremely light and light flow rates). However, it was felt that such traditional indicators may not be accurate with respect to menstrual fluid due to the high viscous and non-homogenous nature of menstrual fluid and the varying effect of the menstrual fluid at different flow rates.

To test an initial theory, sanitary napkins having various combinations of materials typically used for cover layers and surge layers in feminine care products were tested in a small-scale in-vivo test involving about 10 women. The weight of the menstrual fluid taken in by the napkins was determined by subtracting the pre-weight of the napkins from the post-weight of the napkins. This weight was then divided into the total number of hours the product was worn by the user to determine an average menstrual flow rate. Dissection of the products showed if any menstrual fluid remained on the cover layer, between the cover layer and the surge layer, or if the fluid penetrated completely to the absorbent core. A sufficient number of samples were collected in the in-vivo test until the minimum flow rate in ml/hr could be determined for the menstrual fluid to penetrate through the cover layer and surge layer combinations completely into the absorbent core. The mean percent areas of the various surge materials used in the napkins were also noted.

The in-vivo tests revealed that the ability of a particular type of surge material to completely absorb menstrual fluid at a specific flow rate varied with different cover materials. It was also observed that the mean percent area of the surge material was not a consistent indicator of the surge material's performance in a particular cover/surge combination. For example, a surge material with a relatively high mean percent area required a first minimum flow rate for the menstrual fluid to penetrate completely through to the absorbent core with a first type of cover layer material, and the same surge material (same mean percent area) required a different (sometimes lesser) flow rate with a different cover layer material.

An in-vitro test was then conducted to determine if the in-vivo results could be accurately duplicated in a lab or bench test. A controllable syringe pump was used to meter a simulated menstrual fluid onto the same absorbent articles having the same combination of cover and surge materials. The flow rate of the simulated menstrual fluid was varied until the minimum flow rate needed for the simulated menstrual fluid to penetrate completely through the surge material was determined. These in-vitro minimum flow rates were substantially the same as those determined from the in-vivo tests.

Thus, it was found that the type of cover layer material could have a substantial impact on the ability of a particular type of surge layer to absorb and pass menstrual fluid at a particular flow rate, and that such impact could be reliably predicted through in-vitro empirical testing. An accurate in-vitro test method is thus available for determining optimal combinations of materials for use in feminine care absorbent articles, particularly cover layer/surge layer combinations.

The use of a simulated menstrual fluid that accurately reflects the complex nature of actual menstrual fluid is a key consideration. The simulated menstrual fluid used by the applicants is described in U.S. Pat. No. 5,883,231. This fluid is made from red blood cells in an amount between about 10 and about 60 weight percent, egg white in an amount between about 20 and about 50 weight percent, and plasma. The blood is defibrinated swine blood separated by centrifugation into plasma and red blood cells. The egg white was separated from jumbo chicken eggs. It should be appreciated that one skilled in the art may devise any manner of simulated menstrual fluid for use with the present inventive method.

The test for determining an optimal combination of materials with respect to a particular menstrual flow condition for use in a feminine care absorbent article, includes:

a. selecting a subject flow rate corresponding to the flow rate of menstrual fluid for a particular menstrual flow condition. For example, the subject flow rate may be selected to correspond to a heavy, extremely heavy, or gush menstrual flow condition.

b. providing a simulated menstrual fluid to a flow rate controllable metering device. This device may be any suitable liquid metering device, such as a controllable syringe pump. The simulated menstrual fluid should have characteristics that approximate the highly viscous and non-homogenous nature of actual menstrual fluid.

c. dispensing the simulated menstrual fluid onto a first combination of materials at the subject flow rate. The combination of materials may be, for example, a bodyside cover and a subjacent surge layer. Other combinations of various material layers used in the absorbent article may also be tested. The method is not limited to testing any particular combination of materials.

d. observing whether the combination of materials adequately perform their intended purpose in the feminine car product at the subject flow rate. For example, if the selected combination of materials is a bodyside cover and surge layer, the simulated menstrual fluid should be observed to have penetrated from the cover and completely through the surge layer.

e. varying at least one of the materials in the combination and repeating the steps of dispensing the simulated menstrual fluid and observing the performance of the combination of materials. For example, in the cover and surge layer combination, the test may be repeated with different cover layer materials used with the same surge layer material. Likewise, the test may be repeated with the same cover layer material and different surge layer materials, and so forth.

f. selecting an optimal combination of the materials based on their performance when subjected to the simulated menstrual fluid at the subject flow rate. By varying various material combinations in the in-vitro test, an accurate determination of optimal material combinations can be made with a high degree of assurance that the materials will perform just as well in an in-vivo environment.

Once an optimal combination of materials is selected for a given subject flow rate, the same material combination may be retested at a different subject flow rate to determine the combination's utility at different actual menstrual flow conditions. It may be found that, although a particular combination is optimal at one flow rate, it may not be adequate at a different flow rate. Thus, the combination may not be adequate overall if the absorbent article is expected to experience both actual menstrual flow rates. In this case, the present test method is extremely useful in determining a combination of materials that is "optimal" over a particular range of flow rates.

It should be appreciated by those skilled in the art that the present invention testing protocol has beneficial uses in determining optimal material combinations in feminine care products not specifically described herein. It is intended that such uses be considered within the scope and spirit of the invention as set forth in the appended claims.

What is claimed is:

1. An in-vitro method for determining an optimal combination of materials with respect to a particular menstrual flow condition for use in a feminine care absorbent article, said method comprising the steps of:

selecting a subject flow rate corresponding to the flow rate of menstrual fluid for a particular menstrual flow condition;

providing a simulated menstrual fluid to a flow rate controllable metering device;

dispensing the simulated menstrual fluid onto a first combination of materials at the subject flow rate;

observing whether the combination of materials adequately perform their intended purpose in the feminine care product at the subject flow rate;

varying at least one of the materials in the combination and repeating the steps of dispensing the simulated menstrual fluid and observing the performance of the combination of materials; and selecting an optimal combination of the materials based on their performance when subjected to the simulated menstrual fluid at the subject flow rate.

2. The method as in claim 1, wherein at least one of the materials is selected as a cover material.

3. The method as in claim 1, wherein at least one of the materials is selected as a surge material.

4. The method as in claim 1, wherein one of the materials is constant and tested against various other materials to determine the optimal material to be combined with the constant material.

5. The method as in claim 1, further comprising changing the subject flow rate to correspond to a different menstrual flow condition and re-testing the optimal combination of materials at the changed subject flow rate to determine the performance of the combination for different menstrual flow conditions.

6. The method as in claim 1, wherein the subject flow rate is set to correspond to a menstrual flow condition of one of a extremely light flow, light flow, medium flow, heavy flow, extremely heavy flow, and gush flow.

7. The method as in claim 1, wherein said step of determining a subject flow rate comprises selecting a flow rate that represents a range of menstrual flow conditions.

8. The method as in claim 7, wherein the subject flow rate is selected to represent heavy and extremely heavy menstrual flow conditions.

9. The method as in claim 1, wherein the optimal combination of materials is selected based on the combination's ability to reduce leakage of the absorbent article, minimize wetness against a user's skin, and increase menstrual fluid intake.

10. An in-vitro method for determining an optimal combination of cover material and surge material with respect to a particular menstrual flow condition for use in a feminine care absorbent article, said method comprising the steps of:

selecting a subject flow rate corresponding to the flow rate of menstrual fluid for a particular menstrual flow condition;

providing a simulated menstrual fluid to a flow rate controllable metering device;

dispensing the simulated menstrual fluid onto a first combination of cover material and surge material at the subject flow rate;

observing whether the simulated menstrual fluid delivered at the subject flow rate penetrates sufficiently through the cover material and the surge material;

selecting at least one other combination of cover material and surge material and repeating the steps of dispensing the simulated menstrual fluid and observing the degree of menstrual fluid penetration;

rejecting any combination of cover material and surge material that does not adequately allow penetration of the simulated menstrual fluid through the surge material; and selecting an optimal combination of cover material and surge material from the remaining combinations based on the menstrual fluid penetration characteristics of the materials at the subject flow rate.

11. The method as in claim 10, comprising testing the same cover material with different surge materials.

12. The method as in claim 10, comprising testing the same surge material with different cover materials.

13. The method as in claim 10, further comprising changing the subject flow rate to correspond to a different menstrual flow condition and re-testing the optimal combination of cover material and surge material at the changed subject flow rate to determine the performance of the combination for different menstrual flow conditions.

14. The method as in claim 10, wherein the subject flow rate is set to correspond to a menstrual flow condition of one of a heavy flow, extremely heave flow, and gush flow.

15. The method as in claim 10, further comprising disposing an absorbent core layer beneath the surge layer prior to dispensing the simulated menstrual fluid onto the cover material and surge material, and recording the time it takes for the simulated menstrual fluid to penetrate through the surge layer and be absorbed into the absorbent core layer.

16. The method as in claim 15, further comprising locating a transfer material layer between the surge layer and the absorbent core layer.

17. The method as in claim 10, wherein said step of determining a subject flow rate comprises selecting a flow rate that represents a range of menstrual flow conditions.

18. The method as in claim 17, wherein the subject flow rate is selected to represent heavy to extremely heavy menstrual flow conditions.

19. The method as in claim 17, wherein the subject flow rate is selected to represent light to medium menstrual flow conditions.

20. The method as in claim 17, wherein the subject flow rate is selected to represent gush menstrual flow conditions.

21. The method as in claim 10, wherein the optimal combination of cover material and surge material is selected based on the combination's ability to reduce leakage of the absorbent article, minimize wetness against a user's skin, and increase menstrual fluid intake.

* * * * *